United States Patent [19]

Stice

[11] Patent Number: 4,917,099
[45] Date of Patent: Apr. 17, 1990

[54] METHOD AND APPARATUS FOR DIFFERENTIAL LEAD IMPEDANCE COMPARISON

[75] Inventor: John R. Stice, Redmond, Wash.

[73] Assignee: Physio-Control Corporation, Redmond, Wash.

[21] Appl. No.: 219,349

[22] Filed: Jul. 13, 1988

[51] Int. Cl.$^4$ .............................................. A61B 5/04
[52] U.S. Cl. ..................................... 128/696; 128/734
[58] Field of Search ................ 128/734, 419 PT, 696, 128/697, 695, 670

[56] References Cited

U.S. PATENT DOCUMENTS

| | | | |
|---|---|---|---|
| 3,495,584 | 2/1970 | Schwalm | 128/696 |
| 3,559,193 | 11/1967 | Savaglio et al. | 128/696 |
| 3,602,215 | 8/1971 | Parnett | 128/696 |
| 4,141,351 | 2/1979 | James et al. | 128/696 |
| 4,144,892 | 3/1979 | Auerbach | 128/419 PT |
| 4,164,215 | 8/1979 | Finlayson et al. | 128/696 |
| 4,173,221 | 11/1979 | McLaughlin et al. | 128/696 |
| 4,243,044 | 1/1981 | Blancke | 128/696 |
| 4,416,288 | 11/1983 | Freeman | 128/731 |
| 4,459,993 | 7/1984 | Foreman | 128/706 |
| 4,478,223 | 10/1984 | Allor | 128/699 |
| 4,527,567 | 7/1985 | Fischler et al. | 128/419 PT |
| 4,565,201 | 1/1986 | Lass | 128/696 |
| 4,577,639 | 3/1986 | Simon et al. | 128/709 |
| 4,598,281 | 7/1986 | Maas | 128/696 |
| 4,610,254 | 9/1986 | Morgan et al. | 128/419 D |
| 4,619,265 | 10/1986 | Morgan et al. | 128/419 D |
| 4,630,204 | 12/1986 | Mortara | 364/415 |
| 4,630,615 | 12/1986 | Yomtov | 128/734 |
| 4,658,831 | 4/1987 | Reinhard et al. | 128/697 |
| 4,679,144 | 7/1987 | Cox et al. | 364/417 |
| 4,785,812 | 11/1988 | Pihl et al. | 128/696 |

Primary Examiner—Lee S. Cohen
Assistant Examiner—Kennedy J. Schaetzle
Attorney, Agent, or Firm—Christensen, O'Connor, Johnson & Kindness

[57] ABSTRACT

A differential lead impedance comparison apparatus (10) senses lead impedance and compensates for patient-to-patient and electrode variability. A bridge circuit (12) is connected to one end of electrode conductors (22, 24 and 26) in an ECG Leads I configuration. The other end of the conductors (22, 24 and 26) are connected to a patient (18) via electrodes (RA, LA and LL). Leads formed in part by RA, LA and LL and the respective conductors (22, 24 and 26) have lead impedances ($R_b$, $R_a$, and $R_c$). Constant current sources (I1, I2 and I3) are connected to the conductors (22, 24, and 26) and supply constant AC currents ($I_1$, $I_2$ and $I_3$). A first bridge output voltage ($V_M$) is produced by $I_1$ and a combination 32 of $R_a$, $R_b$, and $R_c$. A second bridge output voltage ($V_P$) is produced by $I_2$ and a combination 34 of $R_a$, $R_b$, and $R_c$. A differential amplifier circuit (14) differentially amplifies the $V_M$ and $V_P$ voltages to produce differential voltages ($V_{OM}$ and $V_{OP}$). Demodulators (DM1 and DM2) demodulate $V_{OM}$ and $V_{OP}$ to produce differential impedance voltages ($V_{1M}$ and $V_{1P}$). A first comparator (OA3) changes states and produces a high logic output when $V_{1M}$ equals or exceeds a first threshold level ($V_{TH1}$). A second comparator (OA4) changes states and produces a high logic output when $V_{1P}$ equals or exceeds a second threshold level ($V_{TH2}$). An exclusive OR gate (G1) produces a high logic output ($V_{OUT}$) when one and only one of OA3 or OA4 produce a high logic output.

15 Claims, 3 Drawing Sheets

METHOD AND APPARATUS FOR DIFFERENTIAL LEAD IMPEDANCE COMPARISON

TECHNICAL FIELD

This invention relates to medical diagnostic and therapeutic apparatus employing electrodes applied to the skin of a patient and, more particularly, to apparatus for sensing the integrity of lead connections.

BACKGROUND OF THE INVENTION

It is well known in the medical electrode art that an ECG electrode must make good electrical contact with a patient in order for the electrode to accurately sense the patient's intrinsic ECG rhythm. External ECG electrodes are usually affixed to a patient's skin by the adhesive properties of the electrode, such as by the surface tackiness of an electrolytic gel forming a part of the electrode. When a good electrode-to-skin connection is made, the impedance of the connection is low. If the connection is not good, the connection impedance will be higher than the impedance of a good electrode-to-skin connection. A high ECG electrode-to-skin connection impedance will hinder the electrode's ability to sense the patient's intrinsic ECG rhythm. A sufficiently high electrode-to-skin connection impedance will result in a loss of patient ECG signals to the ECG electrode. In such a situation, ECG monitoring equipment may detect this loss of ECG signals as a loss of cardiac activity in the patient, and alert medical personnel accordingly.

In applications where the ECG signals sensed by the ECG electrodes are used to control other types of equipment, the other equipment may operate improperly due to a loss of the ECG signal. For example, demand mode pacers are designed to apply external pacing pulses to a patient upon demand, i.e., when there is an absence of intrinsic ECG rhythm. If, due to a high ECG electrode-to-skin connection impedance, the ECG signals are blocked from the demand mode pacer, the pacer may sense this as a loss of patient ECG and begin applying pacing pulses to the patient. Obviously, unnecessarily applying pacing pulses to a patient with a normal ECG rhythm may be detrimental to the patient's health.

One method commonly used in the prior art to sense the integrity of the ECG electrode-to-skin connection is to continuously sense an overall lead impedance associated with a particular electrode. The lead impedance associated with an electrode actually comprises several impedances, including an impedance of the electrode conductor, an impedance of the electrode, an electrode-to-skin connection impedance, an internal impedance of the patient, and various other impedances, including those formed by connections of the conductor to the electrode and to other pieces of equipment. Typically, the impedance of the electrode-to-skin connection is the single largest component of the lead impedance associated with a particular electrode. This is especially true where the electrode becomes detached from the patient. Generallly, the prior art senses lead impedance in one of two ways, either by applying a DC signal to the conductors, or by applying a high-frequency AC signal to the conductors. In both prior art methods, the DC or AC signal produces a voltage that is proportional to the lead impedance associated with the electrode. This voltage(s) can then be processed in several ways, but, basically, it is compared to a threshold level, and if it equals or exceeds the threshold level, a poor electrode-to-skin connection (or leads-off condition) is presumed.

One problem associated with the prior art is that the prior art devices sense the lead impedance associated with a particular electrode without regard to the lead impedance associated with other electrodes. As a result, the prior art does not take into account variations between patients or electrode preparation techniques. For example, if a patient has dry skin, the impedance of the electrode-to-skin connections for any electrode attached to that patient will cause the lead impedances associated with those electrodes to be higher than if the electrodes were connected to a patient wth moister skin. Likewise, if a certain type (or brand) of electrode is used on a patient, the impedance of those types of electrodes may cause the lead impedance associated with those electrodes to be different (i.e., higher or lower) than for another type of electrode. Since the prior art senses the lead impedance associated with a particular electrode without regard to other electrodes, the high lead impedance caused, for example, by the dryness of the patient's skin, or by the type of electrode used, may be sensed as a leads-off condition. This may occur even though adequate electrical signals, such as ECG signals, are being received by ECG monitoring equipment attached to the ECG electrodes.

Another problem associated with the prior art concerns the signals used to sense the lead impedance. Some forms of the prior art use DC signals to sense the impedance. Patient movement may cause low-frequency modulation of the DC signals. These low-frequency modulations (in the neighborhood of 1 Hz) may corrupt other electrical signals present, such as the ECG signal. As a result, the ECG monitoring equipment may interpret the corrupted ECG signal as an abnormal patient ECG signal. A problem with the high-frequency AC signals used in the prior art is that, at high frequencies, the capacitance of conductors, such as the ECG conductors, that connect the ECG electrodes to the monitoring equipment becomes significant, and may cause erroneous lead impedance values to be sensed.

As can be readily appreciated from the foregoing discussion, there is a need for a method and apparatus for sensing the integrity of electrode connections generally, and more particularly, the integrity of ECG electrode connections that will take into account, among other factors, patient-to-patient and electrode variability. Such a method and apparatus should discriminate between an electrode leads-off condition and a situation where a high lead impedance is caused by a patient's skin or by a particular type of electrode, for example. Furthermore, such a method and apparatus should not corrupt other electrical signals present, such as patient ECG signals. The present invention is directed to providing such a method and apparatus.

SUMMARY OF THE INVENTION

In accordance with this invention, an apparatus for sensing the integrity of electrode connections is provided. The apparatus comprises: a current source; a receiver; a differential amplifying means; and a comparator. The current source produces first and second AC currents and applies them to first and second electrodes, respectively. A first lead impedance is associated with the first electrode and a second lead impedance is associated with the second electrode. The receiver receives a first voltage produced by the first current and the first lead impedance, and a second voltage produced by the second current and the second lead impedance. The differential amplifier differentially amplifies the first and second voltages to produce first and second differential impedance voltages that are proportional to first and second differences between the first and second lead impedances, respectively. The comparator produces a leads-off output signal when one and only one of the first or second differential impedance voltages equals or exceeds a corresponding first or second threshold level.

In accordance with further aspects of the invention, a method for continuously sensing the integrity of the electrode connections is provided. The method comprises the steps of: producing first and second AC currents; applying the first and second currents to first and second elecrodes; receiving first and second voltages produced by the first and second current signals and the first and second lead impedances; differentially amplifying the first and second voltages to produce first and second differential impedance voltages; and, producing a leads-off output signal when one and only one of the first or second differential impedance voltages equals or exceeds a corresponding first or second threshold level.

As will be readily appreciated from the foregoing summary, the invention provides a method and apparatus for sensing the integrity of lead connections by comparing the differential lead impedances associated with at least two electrodes.

BRIEF DESCRIPTION OF THE DRAWINGS

The foregoing and other features and advantages of this invention will become more readily appreciated as the same becomes further understood by reference to the following detailed description when taken in conjunction with the accompanying drawings, wherein.

DESCRIPTION OF THE PREFERRED EMBODIMENT

In the medical electrode art, there has developed a need for a method and apparatus that senses the integrity of lead connections, such as lead connections between an ECG monitor and a patient, for example, while compensating for, among other factors, patient-to-patient and electrode variability. As will be better understood from the following discussion, the present invention provides these results by sensing a differential lead impedance associated with an electrode and comparing it with a differential lead impedance(s) associated with at least one other active electrode. A lead is defined herein as comprising an electrode and a conductor connected to the electrode. Furthermore, the method of the invention is such that other electrical signals present on the leads, such as patient ECG signals, are not corrupted. As will also be better understood from the following discussion, the present invention is equally suitable for use with single and multiple ECG Lead systems. As is well known in the medical electrode art, a single ECG Lead system employs two active ECG electrodes, whereas a multiple ECG Lead system employs more than two active electrodes (such as four, for example) and combines these active electrodes in various electrode pair combinations to form multiple ECG Leads.

Figure 1:
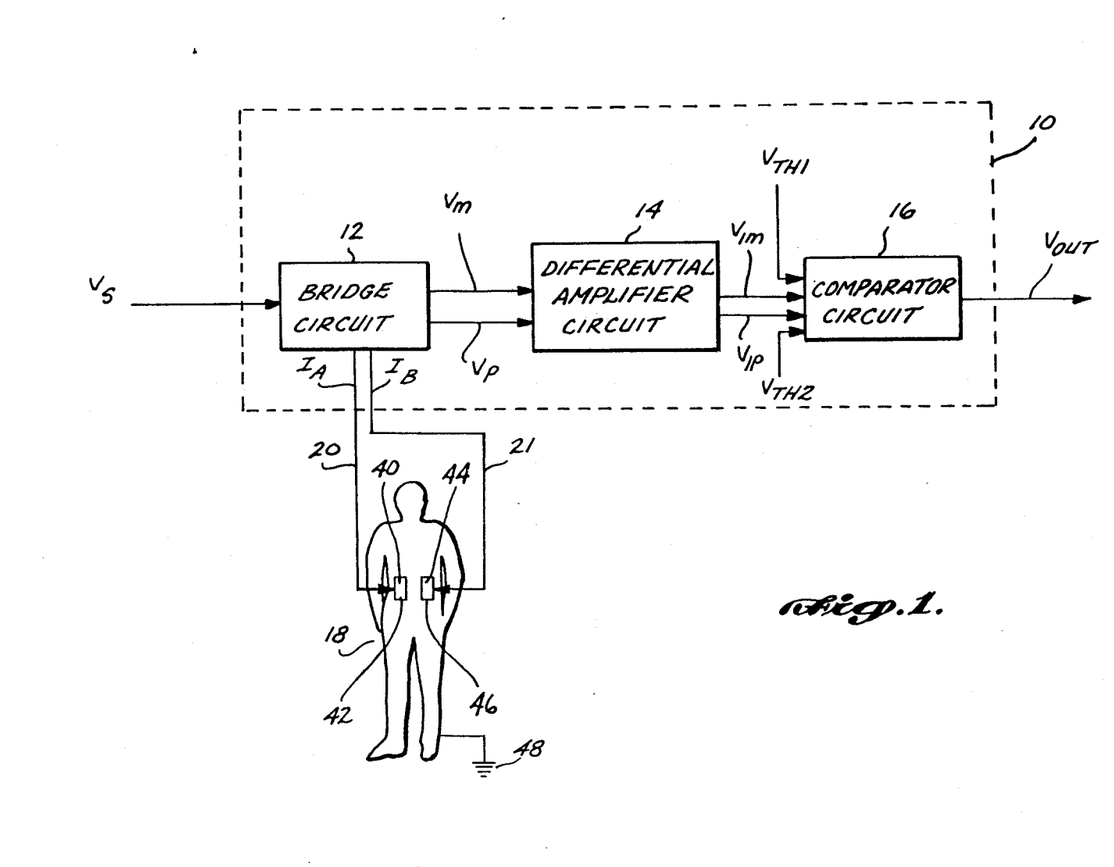
FIG. 1 is a simplified block diagram illustrating broad aspects of a differential electrode impedance comparison apparatus formed in accordance with the present invention.

FIG. 1 is a simplified block diagram of a preferred embodiment of a differential lead impedance comparison apparatus 10 formed in accordance with the present invention. The differential impedance comparison apparatus 10 comprises: a bridge circuit 12; a differential amplifier circuit 14; and, a comparator circuit 16. A first electrode 40 and a second electrode 44 are attached to a patient 18. The patient 18 and the first electrode 40 form a first electrode-to-skin connection 42. The patient 18 and the second electrode 44 form a second electrode-to-patient connection 46. The first electrode 40 is connected to the bridge circuit 12 via a first conductor 20. The first electrode 40 and the first conductor 20 form a first lead. The second electrode 44 is connected to the bridge circuit 12 via a second conductor 21. The second electrode 44 and the second conductor 21 form a second lead. The patient is connected to a reference point 48, such as ground via a reference electrode and a reference conductor, for example. The reference electrode and reference conductor (not shown) form a reference lead. A power supply voltage, designated $V_S$, is applied to the bridge circuit 12. The bridge circuit 12 includes a current source (not shown) that applies a first constant AC current, designated $I_A$, to the first conductor 20 and a second constant AC current, designated $I_B$, to the second conductor 21. As will be better understood from the following discussion, the bridge circuit 12 acts, in part as a receiver, to receive voltages produced by $I_A$ and $I_B$ such that a first bridge output voltage, designated $V_M$, and related to $I_A$, and a second bridge output voltage, designated $V_P$, and related to $I_B$, are supplied to the outputs of the bridge circuit 12. The $V_M$ and $V_P$ voltages are applied to the inputs of the differential amplifier circuit 14. A differential amplifying means, such as the differential amplifier circuit 14, differentially amplifies the $V_M$ and $V_P$ voltages so as to produce a first differential impedance voltage, designated $V_{1M}$, and a second differential impedance voltage, designated $V_{1P}$. The $V_{1M}$ and $V_{1P}$ voltages are applied to an output means, such as the comparator circuit 16. A first threshold level, designated $V_{TH1}$ and a second threshold level, designated $V_{TH2}$, are applied to the comparator circuit 16. A leads-off output signal, designated $V_{OUT}$, is produced by the comparator circuit 16. As will be better understood from the following discusssion, the $V_{OUT}$ signal is produced when either $V_{1M}$ equals or exceeds $V_{TH1}$ or $V_{1P}$ equals or exceeds $V_{TH2}$, but not if both $V_{1M}$ and $V_{1P}$ exceed $V_{TH1}$ and $V_{TH2}$, respectively.

A lead impedance associated with the first lead, designated $Z_1$, comprises impedance of: the first conductor 20, designated $Z_{C1}$; the first electrode 40, designated $Z_{E1}$; the first electrode-to-skin connection 42, designated $Z_{S1}$; and the internal physiology of the patient 18, designated $Z_p$. A lead impedance associated with the first lead, designated $Z_2$, comprises impedances of: the second conductor 21, designated $Z_{C2}$; the second electrode 44, designated $Z_{E2}$; the second electrode-to-patient connection 46, designated $Z_{S2}$; and, $Z_p$. The reference lead has a lead impedance, designated $Z_R$. For ease of discussion, other impedances formed by connections such as the electrode-to-conductor connections and the conductor-to-monitoring apparatus connections are included in the impedances discussed above.

Typically, the most significant factor (i.e., largest single impedance component) of $Z_1$ and $Z_2$ are the electrode-to-skin impedances $Z_{S1}$ and $Z_{S2}$. A poor electrode-to-skin connection 42 or 46 will greatly increase $Z_1$ or $Z_2$, respectvely. Examples of factors contributing to poor electrode-to-skin connections are: dry patient skin or some other high-impedance characteristic of a patient's skin; and, electrode preparation, such as the adhesive properties of the electrode. As will be better understood from the following discussion, the differential impedance comparison apparatus 10 senses signals (such as voltages, for example) that are related to Z1 and Z2, which, as stated above, have several components, including, primarily, the electrode-to-skin impedances ($Z_{S1}$ and $Z_{S2}$), as well as the other impedances, such as the conductor impedances ($Z_{C1}$ and $Z_{C2}$), the electrode impedances ($Z_{E1}$ and $Z_{E2}$) and the patient's internal impedance ($Z_P$).

The $V_M$ voltage is produced by the $I_A$ current and $Z_1$, and the $V_P$ voltage is produced by the $I_B$ current and $Z_2$. The differential amplifier 14 amplifies $V_M$ and $V_P$ voltages and $V_{1P}$ is proportional to a second difference between the $V_M$ and $V_P$ voltages and $V_{1P}$ is proportional to a second difference between the $V_M$ and $p$, and converts the $V_P$ voltage, which is proportional to $Z_2$, into the $V_{1P}$ voltage, which is proportional to the second difference between $V_M$ and $V_P$. As will be better understood from the following discussion, because $V_M$ and $V_P$ are related to $Z_1$ and $Z_2$, and the $V_{1P}$ voltage is proportional to a second difference btween Z1 and Z2. A high impedance common to both the first and second electrodes 40 and 44, such as dry patient skin (i.e., high $Z_{S1}$ and $Z_{S2}$), will affect the values of both $V_{1M}$ and $V_{1P}$. Contrariwise, a high impedance associated with the first electrode 40, which does not affect the second electrode 44, such as a detached electrode 40 (i.e., high $Z_{S1}$), will cause $V_{1M}$ to exceed $V_{1P}$. As discussed above, if the $V_{1M}$ value equals or exceeds $V_{TH1}$, and $V_{1P}$ is less than $V_{TH2}$, then a $V_{OUT}$ signal will be asserted, indicating a leads-off condition. Thus, in this manner, the differential impedance comparison apparatus 10 compensates for common factors between active electrodes.

Figure 2:
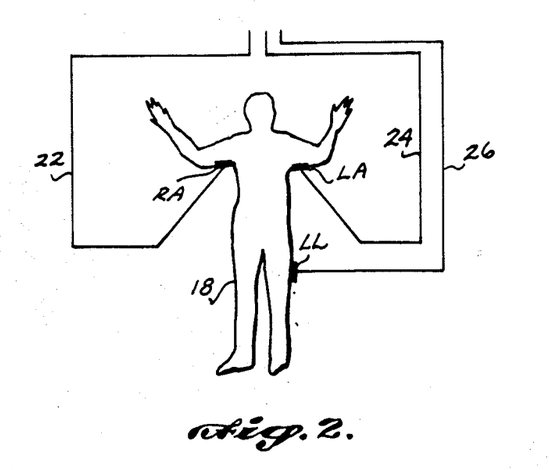
FIG. 2 illustrates an ECG Leads I arrangement suitable for use with the apparatus in FIG. 1.

In one particular embodiment, the present invention can be used with an ECG Leads I electrode arrangement. As is well known in the medical electrode art and as illustrated in FIG. 2, an ECG Leads I arrangement includes two active ECG electrodes and, one reference or common mode ECG electrode. A first active electrode, designated RA, is attached to the right arm of the patient 18, and a second active electrode, designated LA, is attached to the left arm of the patient 18. The common mode, or reference, electrode, designated LL, is attached to the left leg of the patient 18. In the ECG Leads I arrangement, patient ECG signals are sensed by the RA and LA electrodes and applied to the bridge circuit 12 via RA and LA conductors 22 and 24, respectively. The LL electrode is connected to the bridge circuit 12 via a reference, or common mode conductor 26. Obviously, as stated above, the present invention can be practiced, with other ECG Lead arrangements (such as Leads II or Leads III arrangements, for example), and is equally suitable for use with single and multiple ECG Lead systems. That is, the present invention is suitable for use with ECG monitoring apparatus that employ either Leads I, Leads II or Leads III arrangements, for example, or with ECG monitoring apparatus that employ combinations of various Lead arrangements. The invention is also suitable for use with Lead arrangements and combinations not discussed above.

Figure 3:
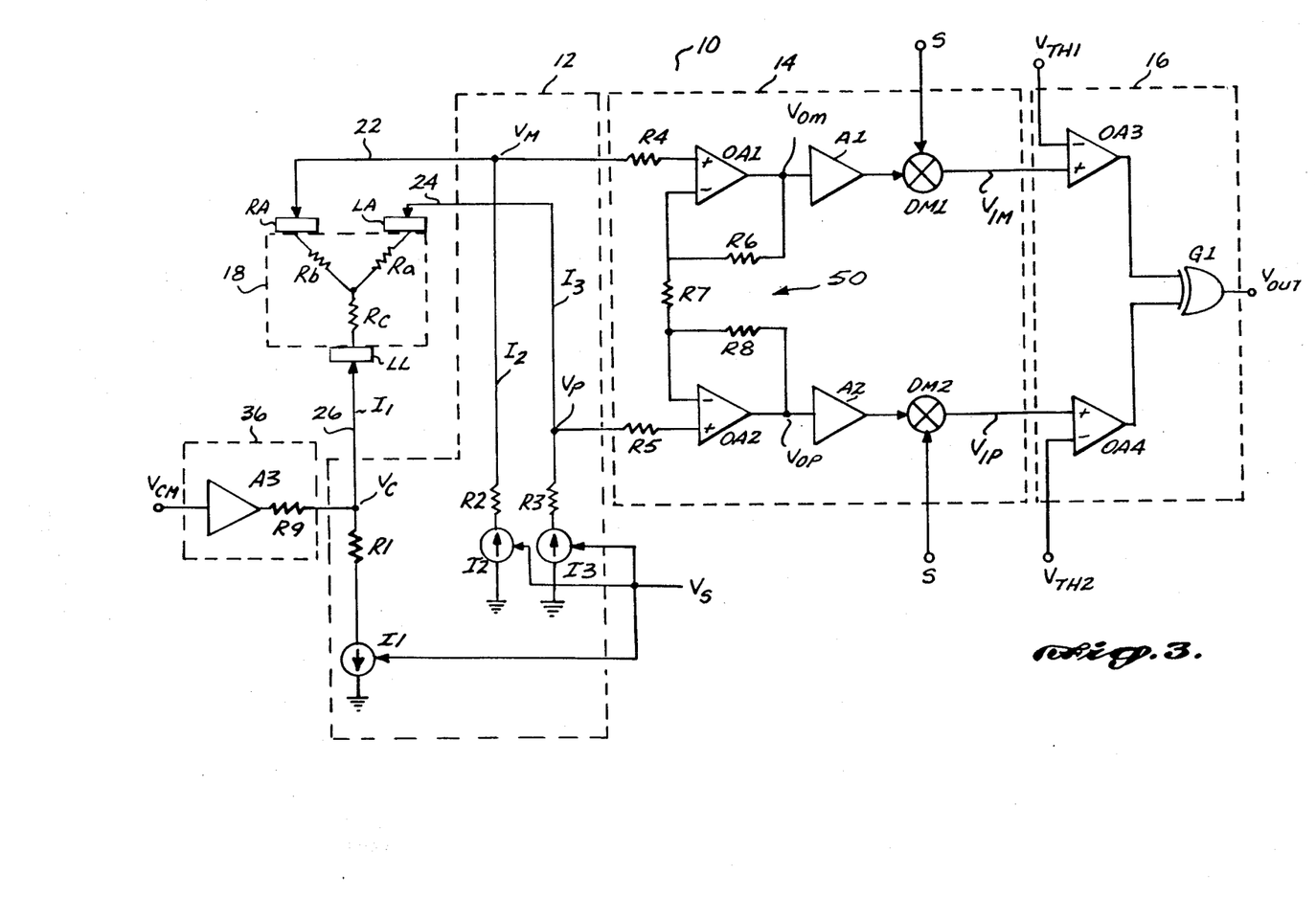
FIG. 3 is a schematic diagram of a preferred embodiment of the apparatus illustrated in FIG. 1; and, FIGS. 4A and 4B are simplified schematic diagrams which more clearly illustrate a portion of the circuit in FIG. 3.

FIG. 3 is a simplified schematic diagram of a preferred embodiment of the differential lead impedance comparison apparatus 10 illustrated in FIG. 1 and discussed above. In the preferred embodiment discussed below, the apparatus 10 is used with the ECG Leads I arrangement (illustrated in FIG. 2). The RA, LA and LL electrodes are attached to the patient 18. The RA, LA and LL electrodes are connected to one of the RA, LA and LL conductors 22, 24 and 26. The other end of the conductors 22, 24 and 26 is connected to the bridge circuit 12. Each conductor and electrode combination forms a lead having an associated lead impedance. More specifically, the RA electrode and conductor 22 combination forms an RA lead that has a lead impedance, designated $R_b$. The LA electrode and conductor 24 combination forms an LA lead that has a lead impedance, designated $R_a$. The LL electrode and conductor 26 combination forms a reference lead that has a lead impedance, designated $R_c$. For ease of illustration and understanding, $R_a$, $R_b$ and $R_c$ are represented as three wye-connected impedances whose noncommon ends are connected to the LA, RA and LL electrodes, respectively. Also, for the same reasons, $R_a$, $R_b$ and $R_c$ are shown as formed within the patient 18. As will be better understood from the following discussion, $R_a$, $R_b$ and $R_c$ each comprise several impedances that are actually located throughout each of the respective RA, LA and LL leads. As will also be better understood from the following discussion, $R_a$, $R_b$, and $R_c$ can be combined so as to represent the actual impedances sensed by the apparatus 10 when used with an ECG Leads I electrode arrangement. That is, $R_a$, $R_b$, and $R_c$ can be combined so as to represent the actual impedances sensed by the apparatus 10 when used with an ECG Leads I electrode arrangement. That is, $R_a$, $R_b$, and $R_c$ can be combined so as to represent the actual immpedance sensed by the apparatus 10 with respect to each of the active electrodes (i.e., RA and LA, illustrated in FIGS. 4A and 4B).

As noted above, each of the lead impedances, $R_a$, $R_b$ and $R_c$, comprise several other impedances. More specifically, $R_a$ includes impedances of: the LA conductor 24; the LA electrode; the patient's internal physiology; an LA electrode-to-skin connection; and, other connections, such as the conductor-to-electrode and conductor-to-monitoring equipment connections. Likewise, $R_b$ and $R_c$ include similar impedances associated with the $R_b$ and $R_c$ leads. As noted above, the impedances of the electrode-to-skin connections for the RA, LA and LL electroes are typically the most significant factors of $R_b$, $R_a$, and $R_c$. Thus, by sensing the lead impedances (i.e., $R_a$, $R_b$ and $R_c$), the apparatus 10 senses the electrode-to-skin impedances as well as the other associated impedances included in $R_a$, $R_b$ and $R_c$.

The bridge circuit 12, illustrated in FIG. 3, comprises: three constant current sources, designated I1, I2 and I3; and, three resistors, designated R1, R2 and R3. The LL electrode is connected (via conductor 26) to the output of a common mode drive circuit 36, discussed below, and to the input of I1 through R1. The output of I is connected to ground. The inputs of I2 and I3 are connected to ground. The output of I2 is connected to one end of R2. The other end of R2 is connected to the RA electrode (via conductor 22) and to one end of a resistor, designated R4, which forms part of the differential amplifier circuit 14 and is discussed below. The output of I3 is connected to one end of R3. The other end of R3 is connected to the LA electrode (via conductor 24) and to one end of a resistor, designated R5, which is also part of the differential amplifier circuit 14 and is discussed below. The $V_S$ power supply voltage, noted above, is applied to I1, I2, and I3 and provides a source of power to I1, I2, and I3. I1, I2 and I3 produce constant AC currents, designated $I_1$, $I_2$ and $I_3$, respectively.

As noted above, the common mode drive circuit 36 is connected to the LL electrode conductor 26. One purpose of the common mode drive circuit 36 is to improve the performance of an ECG system by reducing the effects of undesirable signals, such as noise produced by the $V_S$ voltage. The common mode drive circuit 36 is illustrated for purposes of clarity and completeness and does not form a part of the present invention. Accordingly, the present invention is equally applicable to ECG systems whether or not a common mode drive circuit 36 is used. The common mode drive circuit 36 comprises: a driver amplifier, designated A3; and a resistor, designated R9. A common mode signal, designated $V_{CM}$, is extracted from the RA and LA leads 22 and 24 (connections not shown) and applied to the input of A3. The outptut of A3, designated $V_c$, is applied to the common mode electrode, LL (via conductor 26) through R9. As discussed above, the $V_c$ voltage reduces the effects of such undesirable signals as noise from the $V_s$ voltage.

In accordance with the present invention, $I_2$ and $I_3$ are in phase with $I_1$, and the sum of $I_2$ and $I_3$ is equal to $I_1$. Thus, because the sum of the currents applied to the RA and LA conductors 22 and 24 (i.e., $I_2$ and $I_3$) are balanced by the current in the LL conductor 26 (i.e., $I_1$), $I_1$, $I_2$, and $I_3$ are not detected by other portions of the appartus 10. In one particular embodiment of the present invention, $I_2$ is equal to $I_3$ (i.e., $I_2 = I_3$). For example, $I_2$ and $I_3$ may each have values of 4 $\mu$A and a frequency of 600 Hertz (i.e. $I_2 = I_3 = 4$ $\mu$A @600 Hz), and $I_1$ has a value of 8 $\mu$A and a frequency of 600 Hertz (i.e., $I_1 = 8$ $\mu$A @600 Hz). As will be better understood from the following discussion, the constant AC currents, $I_1$, $I_2$ and $I_3$, and the $R_a$, $R_b$ and $R_c$ impedances produce the $V_M$ and $V_P$ voltages. The $V_M$ and $V_P$ voltages are formed at the RA conductor 22 and LA conductor 24 outputs of the bridge circuit 12, respectively.

Figure 4A:
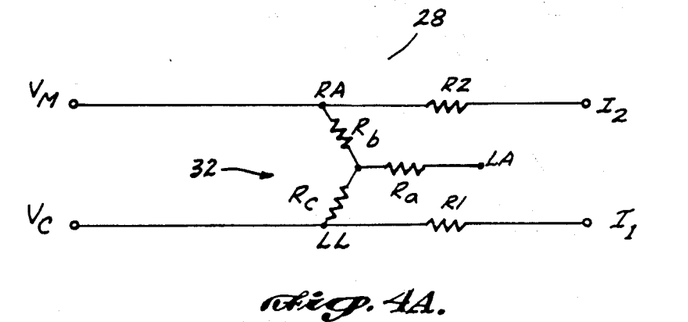
Figure 4B:
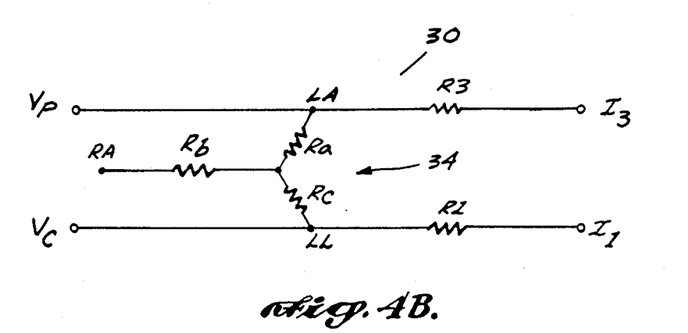

The connections discussed above for the bridge circuit 12 form two, interconnected 4-wire bridge circuits. FIGS. 4A and 4B depict the bridge circuit 12 in a slightly different form so as to more clearly illustrate the two 4-wire bridge circuits. More specifically, FIG. 4A illustrates an RA bridge 28 and FIG. 4B illustrates an LA bridge 30. As can be seen from FIGS. 4A and 4B, both the RA bridge 28 and the LA bridge 30 are 4-wire bridge circuits commonly connected to the LL electrode. The RA bridge 28 measures a first impedance combination 32 of $R_a$, $R_b$, and $R_c$ as formed between the RA and LL electrodes. The LA bridge 30 measures a second impedance combination 34 of $R_a$, $R_b$, and $R_c$ as formed between the LA and LL electrodes. The other various connections illustrated in FIGS. 4A and 4B are identical to the connections discussed above and illustrated in FIG. 3 and are not discussed further.

As is well known in the electrical art, a characteristic of a 4-wire bridge (e.g., the RA bridge 28 and the LA bridge 30) is that the measurements made of a circuit (e.g., the first and second impedance combinations 32 and 34) by such a bridge are independent of the other impedance values in the bridge circuit (e.g., R1, R2, and R3). That is, when a constant current source (e.g., I1, I2 or I3) is connected to the inputs of a 4-wire bridge, a voltage (e.g., $V_M$ or $V_P$) is produced at the outputs of the bridge that varies with the constant current applied to the bridge. As such, the output voltage of the bridge remains proportional to the circuit that is being measured (i.e., the $R_a$, $R_b$ and $R_c$ combination 32 or 34) and is independent of the bridge circuit impedances (i.e., R1, R2 and R3). The significance of this aspect of a bridge as it relates to the bridge circuit 12 of the present invention, is that R1, R2 and R3 can be chosen to have high values, relative to the $R_a$, $R_b$ and $R_c$ impedances, without affecting the measurement of relative to the $R_a$, $R_b$ and $R_c$ combinations 32 and 34. High values for R1, R2 and R3 are desirable because they form a part of a protection network that, for example, protects the differential ECG electrode impedance comparison apparatus 10 from damage caused by the high voltages of defibrillation pulses.

In accordance with the preferred embodiment of the invention, the $V_M$ and $V_P$ voltages co-exist on the RA and LA conductors 22 and 24 with patient ECG signals (not shown). As will be better understood from the following discussion, the $V_M$ and $V_P$ voltages are first differentially amplified and then demodulated to remove the patient ECG signals. The $V_M$ and $V_P$ voltages (illustrated in FIG. 3) and patient ECG signals (not shown) are applied to the differential amplifier circuit 14 which comprises: a first operational amplifier, designated OA1, and a second operational amplifier, designated OA2; an interconnection circuit 50; two buffer amplifiers, designated A1 and A2; two demodulators, designated DM1 and DM2; and, two resistors, designated R4 and R5. The interconnection circuit 50 comprises three resistors, designated R6, R7 and R8. The $V_M$ voltage is applied to the noninverting input of OA1 through R4. The output of OA1 is connected to the input of A1 and to one end of R6. The other end of R6 is connected to the inverting input of OA1 and to one end of R7. The other end of R7 is connected to the inverting input of OA2 and, through R8 to the output of OA2 and to the input of A2. The $V_P$ voltage is applied to the noninverting input of OA2 through R5. A first differential voltage, designated $V_{OM}$, is formed at the output of OA1 and inclues the patient ECG signals in addition to a first difference between the $V_M$ and $V_P$ voltages. A second differential voltage, designated $V_{OP}$, is formed at the output of OA2 and inclues the patient ECG signals in addition to a second difference between the $V_M$ and $V_P$ voltages. As will be better understood from the following discussion, the first and second differences between $V_M$ and $V_P$ are determined in part by R6, R7 and R8. The output of A1 is connected to an input of DM1. The output of DM1 is connected to the noninverting input of an operational amplifier, designated OA3, which forms a part of the comparator circuit 16 discussed below. The output of A2 is connected to an input of DM2. The output of DM2 is connected to the noninverting input of an operational amplifier, designated OA4, which also forms a part of the comparator circuit 16. A sync pulse, designated S, is applied to the clock inputs of DM1 and DM2. As will be better understood from the following discussion, the frequency of the S pulses is the same as the frequency of the $V_M$ and $V_P$ voltages and different from the frequency of the patient ECG signals. The first differential impedance voltage, $V_{1M}$ is formed at the output of DM1. The second differential impedance voltage, $V_{1P}$, is formed at the output of DM2. The $V_{1M}$ and $V_{1P}$ are DC voltages that do not contain the patient ECG signals. As will be better understood from the following discussion, the first and second differential impedance voltages, $V_{1M}$ and $V_{1P}$, form the basis of the differential impedance comparison performed by the present invention. Before discussing the derivation of the $V_{1M}$ and $V_{1P}$ voltages, a brief discussion of the comparison circuit 16 illustrated in FIG. 3 is presented next.

The comparator circuit 16 comprises: a first comparator, designated OA3, and a second comparator, designated OA4; and, a two-input exclusive OR gate, designated G1. The $V_{1M}$ voltage is applied to the noninverting input of OA3. The first threshold level, $V_{TH1}$, is applied to the inverting input of OA3. OA3 changes states and produces a high logic output when $V_{1M}$ equals or exceeds $V_{TH1}$ (i.e., $V_{1M} \geq V_{TH12}$). The $V_{1P}$ voltage is applied to the noninverting input of OA4. The second threshold level, $V_{TH2}$, is applied to the inverting input of OA4. OA4 changes states and produces a high logic output when $V_{1P}$ equals or exceeds $V_{TH2}$ (i.e., $V_{1P} \geq V_{TH2}$). The outputs of OA3 and OA4 are connected to the inputs of G1. G1 produces a high $V_{OUT}$ signal whenever one, and only one, of OA3 or OA4 produces a high logic output (i.e., $V_{1M} \geq V_{TH1}$ and $V_{1P} < V_{TH2}$ or $V_{1M} < V_{TH1}$ and $V_{1P} \geq V_{TH2}$). Thus, a high $V_{OUT}$ signal represents a leads-off condition for the RA or LA lead.

Returning to the differential amplifier circuit 14 and as noted above, the interconnections of OA1 and OA2 through R6, R7 and R8 produce the differential voltages $V_{OM}$ and $V_{OP}$. Such an interconnection of OA1 and OA2 may be found in the first stage of an instrumentation amplifier typically employed in an ECG preamplifier. The $V_{OM}$ and $V_{OP}$ voltages formed at the outputs of OA1 and OA2 are defined by the following equations:

$$V_{OM} = A \cdot V_M - B \cdot V_P + V_{E1} \qquad (1)$$

$$V_{OP} = C \cdot V_P - D \cdot V_M + V_{E2} \qquad (2)$$

where:
$A = (R6+R7)/R7$;
$B = R6/R7$;
$C = (R7+R8)/R7$;
$D = R8/R7$;
$V_{E1}$ represents the patient ECG signal present in the RA lead; and,
$V_{E2}$ represents the patient ECG signal present in the LA lead.

Thus, as discussed above, and as is apparent from Equations (1) and (2), in addition to including patient ECG signals (i.e., $V_{E1}$ and $V_{E2}$), the $V_{OM}$ and $V_{OP}$ voltages are proportional to differences between the $V_M$ and $V_P$ voltages. More specifically, $V_{OM}$ is proportional to a first difference between $V_M$ and $V_P$ (i.e., $AV_M - BV_P$), and $V_{OP}$ is proportional to a second difference between $V_P$ and $V_M$ (i.e., $CV_P - DV_M$), where A, B, C and D are constants derived from R6, R7 and R8.

As discussed above, DM1 and DM2 are clocked by the S pulses so as to remove the ECG signals ($V_{E1}$ and $V_{E2}$) from the $V_{OM}$ and $V_{OP}$ voltages. By expressing the $V_M$ voltage in terms of $I_2$ and the $R_a$, $R_b$ and $R_c$ combination 32 (FIG. 4A), and the $V_P$ voltage in terms of $I_3$ and the $R_a$, $R_b$ and $R_c$ combination 34 (FIG. 4B), the differential impedance voltages, $V_{1M}$ and $V_{1P}$, can be expressed by the following equations:

$$V_{1M} = K_1(A \cdot R_b + 2 \cdot R_c - B \cdot R_a) \qquad (3)$$

$$V_{1P} = K_2(C \cdot R_a + 2 \cdot R_c - D \cdot R_b) \qquad (4)$$

where:
$K_1$ is a product of $I_2$ and the gain of A1;
$K_2$ is the product of $I_3$ and the gain of A2; and,
A, B, C, and D are the constants defined above.

It is clear from the Equation (3) that $V_{1M}$ is proportional to a first differential impedance (i.e., $AR_b - BR_a$), and from Equation (4) that $V_{1P}$ is proportional to a second differential impedance (i.e., $CR_a - DR_b$). It is this differential relationship between the lead impedances ($R_a$ and $R_b$) that forms the basis of the present invention.

As noted above and as will be better understood from the following discussion, high impedances common to both $R_a$ and $R_b$ will not be sensed as a leads-off condition but a high impedance associated with either $R_a$ or $R_b$ (but not both) may be sensed as a leads-off condition if the resulting $V_{1M}$ or $V_{1P}$ voltages are sufficiently high. These determination are made by the comparator circuit 16 discussed above and are further explained by way of examples set forth next.

A high $V_{OUT}$ signal (indicating a leads-off condition) is produced when one and only one of OA3 or OA4 produces a high logic output. Accordingly, a high lead impedance associated with one and only one of the RA or LA leads (i.e., $R_b$ or $R_a$) may produce a high $V_{OUT}$ signal. For example, if an RA leads-off condition exists, i.e., the RA electrode is detached from the patient 18, then $R_b$ will be substantially higher than $R_a$ and $R_c$. As can be seen from Equations (3) and (4), $V_{1M}$ will be much larger than $V_{1P}$ in the above example. Further, if $V_{1M} \geq V_{TH1}$ and $V_{1P} < V_{TH2}$, then $V_{OUT}$ will be high, indicating a leads-off condition. Likewise, in an LA leads-off condition, $R_a$ will be much larger than $R_b$ and $R_c$ and, as can be seen from Equations (3) and (4), $V_{1P}$ will be larger than $V_{1M}$. If $V_{1P} \geq V_{TH2}$ and $V_{1M} < V_{TH1}$, then $V_{OUT}$ will be high, indicating a leads-off condition. Contrariwise, if both $R_a$ and $R_b$ are high due to a high impedance common to both the RA and LA leads, such as a particular patient's dry skin, for example, both $V_{1M}$ and $V_{1P}$ will be high and $V_{OUT}$ will be low. The effect of a detached LL electrode is explained by way of another example. If the LL electrode is detached, $R_c$ will be much greater than $R_a$ and $R_b$, and since $R_c$ is common to both $V_{1M}$ and $V_{1P}$, both $V_{1M}$ and $V_{1P}$ will be high values. Accordingly, $V_{OUT}$ will be low, unless one and only one of $V_{1M}$ or $V_{1P}$ equals or exceeds $V_{TH1}$ or $V_{TH2}$, respectively.

As noted above, in a particular embodiment of the invention, $I_1$, $I_2$, and $I_3$ have a frequency of 600 Hz. Accordingly, the $V_M$ and $V_P$ voltages also have a frequency of 600 Hz. The 600 Hz frequency was selected in the particular embodient discussed above because in many typical ECG preamps (which do not form a part of this invention), the ECG signals are sampled at a sampling freuency of 600 Hz. As a result of the common frequency between $V_M$, $V_P$, and the ECG sampling rate, the $V_M$ and $V_P$ voltages are removed from the sampled patient ECG signals. Thus, the $V_M$ and $V_P$ voltages do not corrupt the patient ECG signals. Furthermore, the relatively low frequency of the $V_M$ and $V_P$ signals (i.e., 600 Hz) reduces the effects of conductor capacitances associated with the electrode conductors 22, 24, and 26. Thus, unlike the prior art devices that employ high frequency AC signals (such as 12 kHz, for example), the sensing of the integrity of the lead connections by the present invention is unaffected by the capacitances of the conductors 22, 24, and 26.

Slight movements of the patient 18 may cause low-frequency modulations of the $V_M$ and $V_P$ voltages. As discussed above, these modulations typically cause problems in the prior art techniques that apply DC signals to the electrode conductors. However, because $V_M$ and $V_P$ are AC voltages in the present invention, these modulations, which are f the order of 1 Hz, appear as close sidebands to the 600 Hz $V_M$ and $V_P$ voltages. These sidebands (i.e., 599 Hz and 601 Hz) are readily filtered out of the patient ECG signal by the 600-Hz ECG sampling process and therefore do not corrupt the ECG signal. These low-frequency modulations remain in the $V_{1M}$ and $V_{1P}$ voltages as slight variations in the amplitudes of the $V_{1M}$ and $V_{1P}$ voltages. Preferably, the $V_{TH1}$ and $V_{TH2}$ values are selected so that these small amplitude variations do not cause G1 to produce a high $V_{OUT}$ signal.

As can be readily appreciated from the foregoing discussion, a method and apparatus that continuously senses and compares the differential lead impedances associated with at least two electrodes, such as ECG electrodes, for example, is provided. Furthermore, the various signals that are produced by the apparatus do not corrupt other electrical signals present, such as patient ECG signals, for example. While a preferred embodiment of the invention has been illustrated and described herein, it is to be understood that, within the scope of the appended claims, various changes can be made. For example, numerous other frequencies can be used for $I_1$, $I_2$, $I_3$, and the S pulses if the ECG sampling rate is also different. Filters could be used to remove the $V_{OM}$ and $V_{OP}$ voltages from the ECG signals instead of selecting a frequency that is the same as the ECG sampling raet. Also, other ECG electrode combinations can be used. Additionally, the invention could be employed in nonmedical electrode applications, such as industrial electrode systems, for example. Hence, the invention can be practiced otherwise than as specifically described herein.

The embodiments of the invention in which an exclusive property or privilege is claimed are defined as follows:

1. An appartus for use with devices employing electrodes that senses the integrity of lead connections comprising:
   (a) a first lead and a current source means coupled to said first lead and a current source means coupled to said first lead having a first lead impedance, a second lead having a second lead impedance and a reference lead having a reference lead impedance, wherein said current source means:
      (i) produces a first AC current and applies said first AC current to said first lead;
      (ii) produces a second AC current and applies said second AC current to said second lead; and,
      (iii) produces a reference AC current and applies said reference AC current to said reference lead;
   (b) a receiver coupled to said first and second leads for receiving a first voltage produced by said first AC current and said first lead impedance and a second voltage produced by said second AC current and said second lead impedance;
   (c) differential amplifying means for differentially amplifying said first and second voltages to produce first and second differential impedance voltages, wherein said first differential impedance voltage is proportional to a first difference between said first and second lead impedances and wherein said second differential impedance voltage is proportional to a second difference between said first and second lead impedances;
   (d) an output means coupled to said differential amplifying means for receiving said first and second differential impedance voltages and producing a leads-off output signal when one and only one of said first and second differential impedance voltages equals or exceeds a corresponding first or second threshold level.

2. The apparatus for sensing the integrity of lead connections claimed in claim 1, wherein said differential amplifying means is a differential amplifying circuit comprising:
   (a) a first amplifier means coupled to said first lead for receiving said first voltage and producing a first differential voltage;
   (b) a second amplifier means coupled to said second lead for receiving said second voltage and producing a second differential voltage; and,
   (c) an interconnecting circuit coupled to said first and second amplifying means.

3. The apparatus for sensing the integrity of lead connections claimed in claim 2, wherein said differential amplifying means further comprises:
   (a) a first demodulator coupled to said first amplifier means or demodulating said first differential voltage and producing said first differential impedance voltage; and,
   (b) a second demodulator coupled to said second amplifier means for demodulating said second differential voltage and producing said second differential impedance voltage.

4. The apparatus for sensing the integrity of lead connections claimed in claim 3, wherein said first and second AC currents are in phase with each other and have the same frequency as each other.

5. The apparatus for sensing the integrity of lead connections claimed in claim 4, wherein said first and second demodulators are synchronously clocked with said frequency of said first and second AC currents.

6. The apparatus for sensing the integrity of lead connections claimed in claim 4, wherein said reference AC current has the same frequency as said first and second AC currents and is in phase with said first and second AC currents.

7. The apparatus for sensing the integrity of lead connections claimed in claim 2, wherein said interconnecting circuit comprises a plurality of resistors.

8. The apparatus for sensing the integrity of lead connections claimed in claim 1, wherein said output means is a comparator circuit comprising:
   (a) a first comparator coupled to receive said first differential impedance voltage from said differential amplifying means, said first comparator producing a first output signal when said first differential impedance voltage equals or exceeds said corresponding first threshold level; and,
   (b) a second comparator coupled to receive said second differential impedance voltage from said differential amplifying means, said second comparator producing a second output signal when said second differential impedance voltage equals or exceeds said corresponding second threshold level.

9. The apparatus for sensing the integrity of lead connections claimed in claim 8, wherein said comparator circuit further comprises a logic gate coupled to receive said first and second output signals from said first and second comparators, said logic gate producing a high logic output when one and only one of said first and second output signals is received by said logic gate.

10. The apparatus for sensing the integrity of lead connections claimed in claim 9, wherein said logic gate is an exclusive OR gate.

11. The apparatus for sensing the integrity of lead connections claimed in claim 1, wherein said current source means comprises:
   (a) a first constant current source means coupled to said first lead such that said first AC current is a constant AC current;
   (b) a second constant current source means coupled to said second lead such that said second AC current is a constant AC current; and,
   (c) a third constant current source means coupled to said reference lead such that said reference current is a constant AC current whose amplitude is equal to the sum of the amplitudes of said first and second AC currents.

12. The apparatus for sensing the integrity of lead connections claimed in claim 11, wherein said current source means and said receiver form a bridge circuit.

13. A method for sensing the integrity of lead connections comprising the steps of:
   (a) producing first and second AC currents and a reference AC current;
   (b) applying said first AC current to a first lead having a first lead impedance, applying said second AC current to a second lead having a second lead impedance and applying said reference AC current to a reference lead having a reference lead impedance;
   (c) receiving a first voltage produced by said first current and said first lead impedance and receiving a second voltage produced by said second current and said second lead impedance;
   (d) differentially amplifying said first and second voltages to produce a first differential impedance voltage and a second differential impedance voltage, wherein said first differential impedance voltage is proportional to a first difference between said first and second lead impedances and said second differential impedance voltage is proportional to a second difference between said first and second lead impedances; and,
   (e) producing a leads-off output signal when one and only one of said first or second differential impedance voltages equals or exceeds a corresponding first or second threshold level.

14. The method for sensing the integrity of lead connections claimed in claim 13, wherein said step of differentially amplifying said first and second voltages comprises the steps of:
   (a) differentially amplifying said first voltage to produce a first differential voltage;
   (b) demodulating said first differential voltage to produce said first differential impedance voltage;
   (c) differentially amplifying said second voltage to produce a second differential voltage; and,
   (d) demodulating said second differential voltage to produce said second differntial impedance voltage.

15. The method for sensing the integrity of lead connections claimed in claim 14, wherein said step of producing a leads-off signal comprises the steps of:
   (a) comparing said first differential impedance voltage with said coresponding first threshold level; and,
   (b) comparing said second differential impedance voltage with said corresponding second threshold level.

* * * * *